(12) United States Patent
Anderson et al.

(10) Patent No.: US 6,329,163 B1
(45) Date of Patent: *Dec. 11, 2001

(54) ASSAYS FOR DETECTING β-SECRETASE INHIBITION

(75) Inventors: John P. Anderson, San Francisco; Kirsten L. Jacobson-Croak, San Bruno; Sukanto Sinha, San Francisco, all of CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/054,334

(22) Filed: Apr. 2, 1998

Related U.S. Application Data (63) Continuation of application No. 08/485,152, filed on Jun. 7, 1995, now abandoned.

(51) Int. Cl.[7] .............................. C12Q 1/37; G01N 33/53
(52) U.S. Cl. ................... 435/23; 435/4; 435/24; 435/7.1; 435/7.95; 436/518
(58) Field of Search .............................. 435/7.1, 7.2, 23, 435/70.21, 240.27, 961, 4, 24, 7.95; 436/516, 518, 529, 530, 547, 548, 155, 161

(56) References Cited

U.S. PATENT DOCUMENTS 5,200,339 * 4/1993 Abraham et al. .
5,424,205 * 6/1995 Dovey .

FOREIGN PATENT DOCUMENTS

| 0 576 152 | 5/1993 | (EP) . |
| WO 91/13904 | 9/1991 | (WO) . |
| WO 92/03542 | 3/1992 | (WO) . |
| WO 92/07068 | 4/1992 | (WO) . |

OTHER PUBLICATIONS

Simian et al, J. Biol. Chem, 268(22):16602–16609, 1993.*
Glenner et al Advances in Behavioral Biology vol. 44, Alzheimer's + Parkinson's Diseases, Plenum Press, NY 1993.*
Savage et al Neuroscience 60(3):607–619, 1994.*
Evin et al, Amyloid: Int. J. Exp. Clin. Invest 1: 263–280, 1994.*
Elvin, G., et al., "Alzheimer's disease amyloid precursor protein (Ap p): proteolytic processing, secretases and A4 amyloid production," *Amyloid: Int. J. Exp. Clin. Invest.*, 1:263–280 (1994).
Matsumo, A., et al., "$Ca^{2+}$–Dependent 68–Kilodalton Protease in Familial Alzheimer's Disease Cells Cleaves the n–Terminus of –Amyloid," *Biochemestry*, 33:3941–3948 (1994).
Citron, M., et al., "Generation of Amyloid Protein from Its Precursor is Sequence Specific," *Neuron.*, 14:661–670 (1995).
Matsumoto, A., et al., "Molecular cloning of human cDNA with a sequence hihgly similar to that of the dihydrofolate reductase gene in brain librairies derived from Alzheimer'disease patients," *Eur. J. Biochem.*, 230:337–343 (1995).
Brown, A., et al., "Evaluation of Cathespins d and G and EC 3,4,24,15 as Candidate –Secretase Proteases Using Peptide and Amyloid Precursor Protein Substrates," *J. Neurochem.* vol. 66. No. 6, 2436–2445 (1996).
Tagawa, et al., "Alzheimer's disease amyloid –cliiping enzyme (APP secretase): Identification, purification, and characterization of the enzyme," *Biochemical and Biophyusical Research Communication.*, vol. 177. No. 1,377–387, especially pp. 379–380 (1991).
Sambamurti, et al., "Evidence for intracellular cleavage of the Alzheimer's amyloid precursir in PC12 cells," *Journal of Neuroscience Research.*, 33:319–328, entire document.
Nelson, et al., "Identification of a Chymotrypsin–Like Mast Cell Protease in Rat Brain Capable of Generating the N–Terminus of the Alzheimer Amyloid –Protein," *Journal of Neurochemistry.*, vol. 61, No. 2, 567–577, especially 571–572 (1993).
Glenner, et al., "Advances in Behavioral Biology." *Alzheimer's and Parkinson'Diseases: Recent Developments.* Plenum Press, NY, 44:127–130, expecially p. 129, third and seventh paragraphs., (1995).
Haass, Christian, et al., "Amyloid –Peptide is Producted by Cultured Cells Dring Normal Metabolism," *Nature*, 359:322–325 (1992).
Kang, Jie, et al., "The Precursor of Alzheimer's Disease Amyloid A4 Protein Resembles a Cell–Surface Receptor." *Nature*, 325:733–736 (1987).
Selkoe, Dennis J., "Cell Biology of the Amyloid –Protein Precursor and the Mechanism of Alzheimer's Disease," *Annual Review Cell Biology*, 373–403.
Seubert, Paul, et al., "Isolation and Quantification of Soluble Alzheimer's –Peptide from Biological Fluids," *Nature.* 359:325–327 (1992).
Savage, M., et al., *Neuroscience*, 60(3):607–619 (1994).
Simon, R., et al., *JBC.* 268(22):16602–16609 (1993).

* cited by examiner

*Primary Examiner*—Patricia A. Duffy
(74) *Attorney, Agent, or Firm*—Townsend and Townsend and Crew LLP; Carol A. Stratford (57) ABSTRACT

Compositions comprising a novel protease capable of cleaving β-amyloid precursor protein on the amino-terminal side of the β-amyloid peptide therein are provided. The protease is designated β-secretase. The β-secretase may be used in screening assays to identify β-secretase inhibitors, or the β-secretase is combined with a suitable polypeptide substrate and cleavage of the substrate determined in the presence and absence of the test substance.

15 Claims, 6 Drawing Sheets

```
   1     ATGAAAACTGAAGAAGGTAAACTGGTAATCTGATTAACGGCGATAAAGGCTATAACGGTCTCGCTGAAGTCGGTAAG
   1  →  MetLysThrGluGluGlyLysLeuValIleTrpIleAsnGlyAspLysGlyTyrAsnGlyLeuAlaGluValGlyLys
  79  →  AAATTCGAGAAAGATACCGGAATTAAAGTCACCGTTGAGCATCCGGATAAACTGGAAGAGAAATTCCCACAGGTTGCG
  27  →  LysPheGluLysAspThrGlyIleLysValThrValGluHisProAspLysLeuGluGluLysPheProGlnValAla
 157     GCAACTGGCGATGGCCCTGACATTATCTTCTGGGCACACGACCGCTTTGGTGGCTACGCTCAATCTGGCTGTTGGCT
  53  →  AlaThrGlyAspGlyProAspIleIlePheTrpAlaHisAspArgPheGlyGlyTyrAlaGlnSerGlyLeuLeuAla
 235     GAAATCACCCCGGACAAAGCGTTCCAGGACAAGCTGTATCCGTTTACCTGGGATGCCGTTACACGGCAAGCTG
  79  →  GluIleThrProAspLysAlaPheGlnAspLysLeuTyrProPheThrTrpAspAlaValArgTyrAsnGlyLysLeu
 313     ATTGCTTACCCGATCGCTGTTGAAGCGTTATCGCTGATTTATAACAAAGATCTGCCGAACCCGCCAAAACCTGG
 105  →  IleAlaTyrProIleAlaValGluAlaLeuSerLeuIleTyrAsnLysAspLeuProAsnProProLysThrTrp
 391     GAAGAGATCCCGGCGCTGGATAAAGAACTGAAAGCGAAAGGTTATCGCTGATTTCAACCTGCAAGAACCGTAC
 131  →  GluGluIleProAlaLeuAspLysGluLeuLysAlaLysGlyTyrLysAlaLeuMetPheAsnLeuGlnGluProTyr
 469     TTCACCTGGCCGCTGATTGCTGCTGCGCAGAAGCTGGGTCTATGCGTTCAAGTATCGTTAGCGTTGACACACAGAC
 157  →  PheThrTrpProLeuIleAlaAlaGlyAlaLysLeuGlyGlyTyrAlaPheLysTyrGluAsnGlyLysTyrAspVal
 547     GGCGTGGATAACGCTGGCCGCAGAAGCTGCCTTTAATAAAGGCGAAACAGCGATGACCATCAACGGCCCGTGGCATGTCC
 183  →  GlyValAspAsnAlaGlyArgAlaGlyAlaGlyAlaLeuAlaPheAsnLysGlyGluThrAlaMetThrIleAsnAlaAsp
 625     ACCGATTACTCCATCGACAGCAAAGTGAATTATGTGTAACGTCGTGCCAGACCTTCAAGGTCAACCATCCAACCGTTCGTT
 209  →  ThrAspTyrSerIleAspSerLysValAsnTyrValThrValLeuProThrPheLysGlyGlnProSerLysProPheVal
 703     AACATCGACACCAGCAAAGTCTGAGCGCAGTATTAACGCCGCAGTCGAACAAAGACAAACCGCTGGGCGAAAGAGTTCCTGAAAACTATCTGCTG
 235  →  AsnIleAspThrSerLysValAsnTyrGlyValThrValAsnAlaAlaSerProAsnLysGluAlaLysGluPheLeuGluAsnTyrLeuLeu
 781     GGCGTGCTGAGCGCAGTATTAACGCCGCAGTCGAACAAAGACAAACCGCTGGGCGAAAGAGTTCCTGAAAACTATCTGCTG
 261  →  GlyValLeuSerAlaGlyIleLeuAlaValAlaAsnAlaLysAspLysProLeuGlyLysAlaAlaLeuSerTyrGluGluLeu
 859     ACTGATGAAGGTCTGAAGCGGTTAATAAACAGCGGTATAAAGACGAAAAATGCCGATAATCAAGGTCTTACGAGGAAGAGTTG
 287  →  ThrAspGluGlyLeuAsnAlaLysAsnLysGlyLeuIleIleMetProAsnIleProGlnMetSer
 937     GCGAAAGATCCACGTCTGGAAGCGCAGTATTGCCGCAGCTGCACCATCAACGCCCCGCGTCGTCAGACTGTCGATGAAGCCCTGAAAGAC
 313  →  AlaLysAspProArgIleAlaValArgThrAlaValIleAsnAlaAlaSerGlyArgGlnThrValAspGluAlaLeuLysAsp
1015     GCTTTCTGGTATGCCGTGCAGTGCCCGCAGCTGCCATGAAGAAAATAGCGGCCCAGAGGTGAAACATCCGAACATCCCGAGATGTCC
 339  →  AlaPheTrpTyrAlaValArgThrAlaValIleAsnAlaAlaSerGlyArgGlnThrValAspGluAlaLeuLysAsp
1093     GCGCAGACTAATTCGAGCTCGGTACGCCGGGATCCATCGAGGTAGGGCGACCGAGGACTGACCACTCGACCA
 365  →  AlaGlnThrAsnSerSerValProGlyArgGlySerIleGluGlyArgAlaArgAlaAspArgGlyLeuThrThrArgPro
```

*FIG._6A*

```
1171        GGTTCTGGGTTGACAAATATCAAGAACGGAGGAGATCTCTGAAGTGAATCTGGATGCAGAATTCCGACATGACTCAGGA
 391 →      GlySerGlyLeuThrAsnIleLysThrGluGluIleSerGluValAsnLeuAspAlaGluPheArgHisAspSerGly

1249        TATGAAGTTCATCATCAAAAATTGGTGTTCTTTGCAGAAGATGTGGGTTCAAACAAAGGTGCAATCATTGGACTCATG
 417 →      TyrGluValHisHisGlnLysLeuValPheAlaGluAspValGlySerAsnLysGlyAlaIleIleGlyLeuMet

1327        GTGGGCGGTGTTGTCATAGCGACAGTGATCGTCATCACCTTGGTCTGATGCTGAAGAAGAAACAGTACACATCCATTCAT
 443 →      ValGlyValValIleAlaThrValIleValIleThrLeuValMetLeuLysLysLysGlnTyrThrSerIleHis

1405        CATGGTGTGGTGGAGGTTGACGCCGCTGTCACCCCAGAGGAGCGCCACCTGTCCAAGATGCAGGAGAACGGCTACGAA
 469 →      HisGlyValValGluValAspAlaAlaValThrProGluGluArgHisLeuSerLysMetGlnGlnAsnGlyTyrGlu

1483        AATCCAACCTACAAGTTCTTTGAGCAGATGCAGAACTAG...
 495 →      AsnProThrTyrLysPhePheGluGlnMetGlnAsn...
```

ASSAYS FOR DETECTING β-SECRETASE INHIBITION

This application is a continuation of U.S. patent application Ser. No. 08/485,152, filed Jun. 7, 1995, now abandoned.

BACKGROUND OF THE INVENTION

1. Field of the Invention

The present invention relates generally to the cleavage of β-amyloid precursor protein to produce β-amyloid peptide. More particularly, the present invention relates to isolated and purified compositions containing an enzyme responsible for such cleavage (β-secretase) and assays for identifying inhibitors of β-secretase.

Alzheimer's disease is characterized by the presence of numerous amyloid plaques and neurofibrillary tangles (highly insoluble protein aggregates) present in the brains of Alzheimer's disease patients, particularly in those regions involved with memory and cognition. β-amyloid peptide is a major constituent of amyloid plaque which is produced by cleavage of β-amyloid precursor protein. It is presently believed that a normal (non-pathogenic) processing of the β-amyloid precursor protein occurs via cleavage by a putative "α-secretase" which cleaves between amino acids 16 and 17 of the β-amyloid peptide region within the protein. It is further believed that pathogenic processing occurs in part via a putative "β-secretase" which cleaves at the amino-terminus of the β-amyloid peptide region within the precursor protein. Heretofore, however, the existence of β-secretase has not been confirmed.

The identification, isolation, and characterization of novel biological molecules having unique activities is generally useful. For example, novel enzymes can be used to catalyze reactions of a type associated with their class. In particular, novel proteases can be used to cleave proteins for a variety of purposes, and the availability of new proteases provides unique capabilities. In addition to such uses associated with enzymes in general, the identification, isolation, and purification of the putative β-secretase enzyme would permit chemical modeling of a critical event in the pathology of Alzheimer's disease and would allow the screening of compounds to determine their ability to inhibit β-secretase activity.

For these reasons, it would be desirable to isolate, purify, and characterize the enzyme responsible for the pathogenic cleavage of β-amyloid precursor protein at the amino-terminus of the β-amyloid peptide region. In particular, it would be desirable to utilize such an enzyme (referred to hereinafter as β-secretase) in methods for screening candidate drugs for the ability to inhibit the activity of β-secretase in in vitro systems. It would be particularly desirable if such screening assays could be performed in a rapid format which would permit the screening of large numbers of test drugs in automated fashion.

2. Description of the Background Art

β-amyloid precursor protein is expressed in three differently-spliced forms of 695, 751, and 770 amino acids, and "normal" processing involves proteolytic cleavage at a site between residues $Lys^{16}$ and $Leu^{17}$ in the β-amyloid peptide. Kang et al. (1987) *Nature* 325:773–776. Soluble β-amyloid peptide which has been cleaved at the putative β-secretase site has also been found in the culture medium of non-diseased cells (Haass et al. (1992) *Nature* 359:322–325) and in CSF from healthy humans and animals (Seubert et al. (1992) *Nature* 359:325–327). The possible existence of the putative β-secretase is discussed in, for example, Selkoe, "Cell Biology of the Amyloid β-Protein and the Mechanism of Alzheimer's Disease," in *Annual Review of Cell Biology,* Spudich et al., eds., Annual Review, Inc., Palo Alto, Calif., vol. 10, 1994.

SUMMARY OF THE INVENTION

Figure 1:
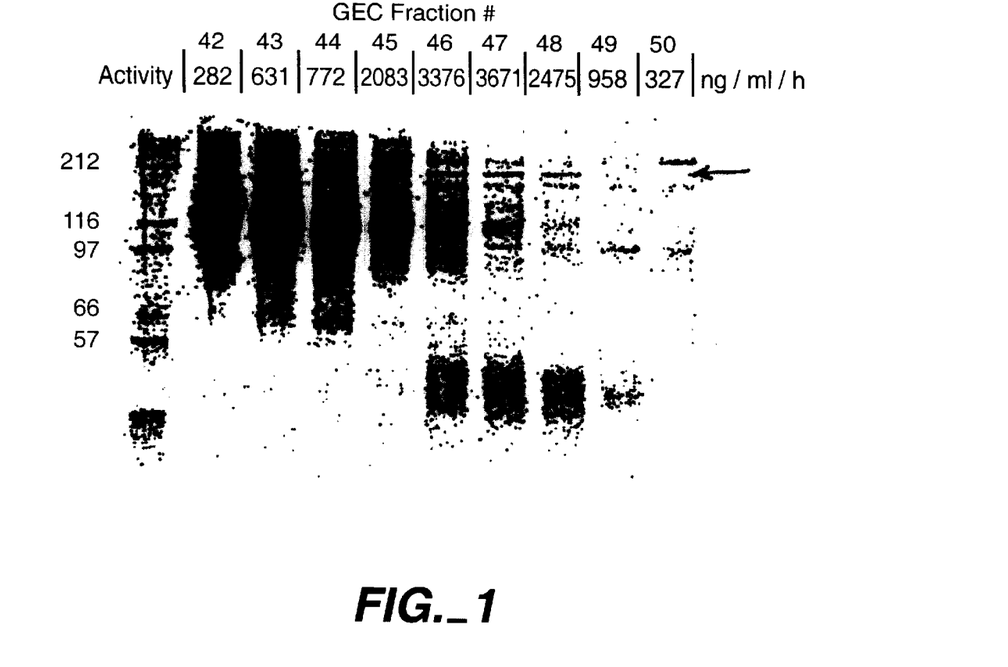
FIG. 1 shows the elution profile of β-secretase purified from human 293 cells produced by gel exclusion chromatography on Superdex 200.
Figure 2:
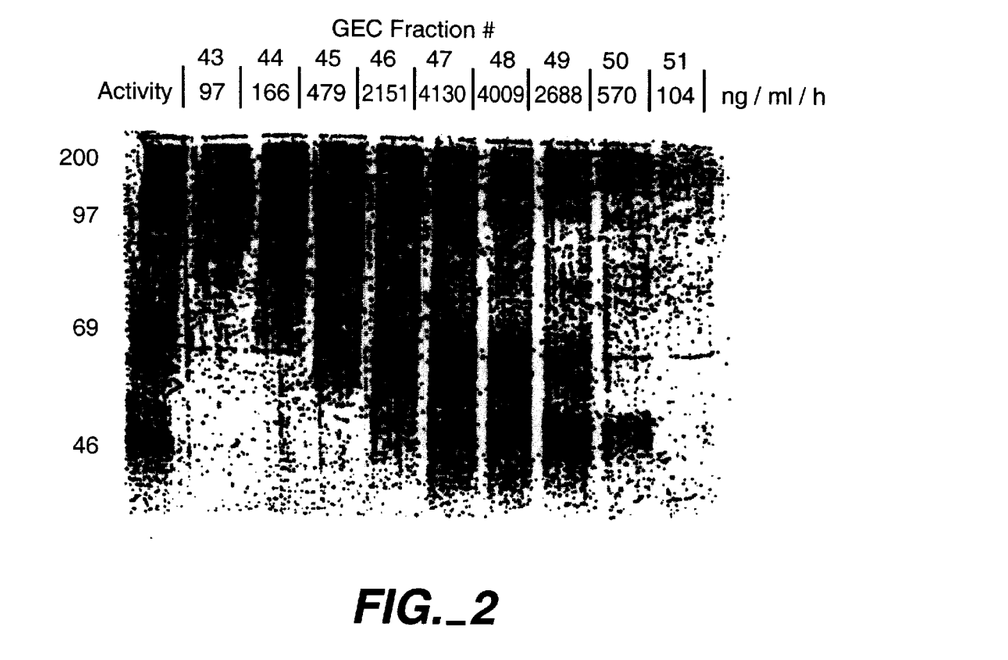
FIG. 2 is a similar elution profile shown for β-secretase purified from human brain.

The present invention provides an assay which utilizes a novel β-secretase composition comprising an isolated and purified enzyme which cleaves β-amyloid precursor protein (APP) at the amino-terminus of β-amyloid peptide (βAP) within APP, referred to hereinafter as "β-secretase activity." The compositions of the present invention will generally have a β-secretase activity which is at least 5-fold, preferably 10-fold, and more preferably 100-fold greater than that of a solubilized but unenriched membrane fraction from human 293 cells. The β-secretase enzyme is characterized by (1) a molecular weight in the range from 260 kD to 300 kD, (2) a gel pattern as shown in FIG. 1 or 2 (discussed in more detail in the Experimental section hereinafter), (3) a net negative charge at pH 5 and a net negative charge at pH 7.5, and (4) binding to wheat germ agglutinin.

The methods of the present invention allow identification of test substances which inhibit proteolytic cleavage of APP resulting from the novel β-secretase. The method comprises exposing a polypeptide comprising the β-secretase site of APP (located at the amino-terminus of the βAP region within APP) to an at least partially purified β-secretase in the presence of the test substance under conditions such that the β-secretase would be expected to cleave the polypeptide into an amino-terminal fragment and a carboxy-terminal fragment in the absence of test substance which inhibits such cleavage. Test substances which inhibit such cleavage are thus identified as having β-secretase inhibition activity. Such test methods preferably employ the β-secretase compositions described above. Usually, generation of the amino-terminal fragment and/or the carboxy-terminal fragment is detected by an antibody specific for the carboxy end of the amino-terminal fragment or the amino end of the carboxy-terminal fragment. The polypeptide substrate for the β-secretase preferably comprises at least the 125 carboxy-terminal amino acids of APP, and may comprise a fusion polypeptide including an amino-terminal portion having a binding epitope. Use of such a fusion polypeptide as the β-secretase substrate facilitates detection of cleavage by capture of the amino-terminal portion and labelling of the amino-terminal portion.

BRIEF DESCRIPTION OF THE DRAWINGS

SW-192 antibody bound to a reporter is utilized, which antibody recognizes the carboxy-terminus of the Swedish mutation of APP. Wild-Type Sequence=SEQ ID NO:5; Swedish Sequence=SEQ ID NO:6.

FIG. 5 illustrates APP 638 which is a recombinantly expressed form of APP truncated after βAP (Aβ). APP 638 may be used in a β-secretase assay where the βAP peptide is cleaved and the carboxy-terminus of the amino-terminal fragment of APP 638 recognized by 192 antibody in either a Western blot or ELISA assay. The carboxy terminal βAP fragment can also be measured using a 3D6/266 assay. Wild-Type Sequence=SEQ ID NO:5; Swedish Sequence= SEQ ID NO:6.

DESCRIPTION OF THE PREFERRED EMBODIMENT

The present invention provides a novel protease which cleaves the β-amyloid precursor protein (APP) at the amino-terminus of the β-amyloid peptide (βAP) therein. It is believed that this protease is the putative β-secretase responsible for the pathogenic processing of APP to produce βAP in βAP-related conditions, such as Alzheimer's disease, Down's syndrome, HCHWA-D, and the like. Thus, the novel protease of the present invention will be referred to hereinafter as "β-secretase." The β-secretase of the present invention will be useful as a protease in in vitro and in vivo systems where proteases may generally find use. For example, β-secretase may be used to cleave or attempt to cleave proteins in order to characterize, process, modify, or otherwise react with the protein as a substrate. Thus, β-secretase will have general utility as a proteolytic chemical reagent in a wide variety of chemical reactions and systems. In addition, the β-secretase of the present invention will have a specific utility in the performance of screening assays to identify β-secretase inhibitors, i.e., test compounds which are able to inhibit the proteolytic cleavage of APP in the presence of β-secretase. Such assays will be described in detail below.

As used herein, "β-amyloid precursor protein" (APP) refers to a polypeptide that is encoded by a gene of the same name localized in humans on the long arm of chromosome 21 and that includes a βAP region (defined below) within its carboxyl third. APP is a glycosylated, single-membrane-spanning protein expressed in a wide variety of cells in many mammalian tissues. Examples of specific isotypes of APP which are currently known to exist in humans are the 695-amino acid polypeptide described by Kang et al. (1987) Nature 325:733–736, which is designated as the "normal" APP. A 751-amino acid polypeptide has been described by Ponte et al. (1988) Nature 331:525–527 and Tanzi et al. (1988) Nature 331:528–530. A 770-amino acid isotype of APP is described in Kitaguchi et al. (1988) Nature 331:530–532. A number of specific variants of APP have also been described having point mutations which can differ in both position and phenotype. A general review of such mutations is provided in Hardy (1992) Nature Genet. 1:233–234. A mutation of particular interest is designated the "Swedish" mutation where the normal Lys-Met residues at positions 595 and 596 are replaced by Asn-Leu. This mutation is located directly upstream of the normal β-secretase cleavage site of APP, which occurs between residues 596 and 597 of the 695 isotype.

As used herein, "β-amyloid peptide" (βAP) refers to the approximately 43 amino acid peptide which comprises residues 597–640 of the 695 amino acid isotype of APP. BAP is produced by processing of the APP including cleavage at both the amino-terminus and carboxy-terminus of the region. It is believed that the β-secretase of the present invention is responsible for cleavage of APP at the amino-terminus of βAP in normal and pathogenic processing of APP in human cells. β-secretase has been characterized in a number of respects, as described in detail in the Experimental section below. β-secretase has a molecular weight in the range from 260 kD to 300 kD, with a tentative molecular weight of 280 kD determined by gel exclusion chromatography in 0.2% hydrogenated Triton X-100. β-secretase will bind to wheat germ agglutinin but not to concanavalin A. It has been found to have a net negative charge at pH 5 (where it does not bind to a cationic exchange material) and a net negative charge at pH 7.5 (where it binds to an anion exchange material). The β-secretase of the present invention will cleave both wild-type (normal) and the Swedish mutation of APP at the putative β-secretase cleavage site on the immediate amino-terminal side of the βAP fragment, and has been found to have a higher proteolytic activity with respect to the Swedish form of APP. Proteolytic activity appears to be at its peak at a pH from 5 to 5.5, with very low activity at pH 7.5 and above. β-secretase is resistant to many known protease inhibitors (see Table 1 in the Experimental section below). β-secretase appears to recognize only those polypeptide substrates which have retained a substantial number of residues upstream and downstream from the cleavage site (from either the wild-type, Swedish, or other mutated form) of APP, with an oligopeptide analog including 17 residues upstream and 16 residues downstream from the cleavage site (with a total of 33 amino acids) being resistant to cleavage by β-secretase.

The β-secretase of the present invention will be provided in an isolated and purified form. By "isolated and purified," it is meant that the β-secretase has been either (1) isolated and at least partially purified from a natural source, such as human brain tissue or human 293 cells (as described in detail in the Experimental section below) or (2) is produced recombinantly and synthetically. At present, as neither the amino acid sequence nor the nucleic acid sequence of the β-secretase gene have been determined, it is preferred that β-secretase be obtained from cellular sources using known protein purification techniques. Contaminating proteins may be removed from the β-secretase co-positions by specific techniques, including serial lectin chromatography on agarose-bound succinylated-wheat germ agglutinin (SWGA) and agarose-bound lentil lectin (LCA). These lectins, although partly binding β-secretase activity, preferentially bind other contaminating proteins in the purified fractions, and thus allow increased enrichment of the β-secretase activity. The β-secretase will be isolated and purified to an extent sufficient to increase the β-secretase activity in the resulting composition to a useful level. In particular, the β-secretase preparations of the present invention will have sufficient activity to cleave APP and APP-containing polypeptides as described in the Experimental section below. Preferably, the β-secretase compositions of the present invention will have an activity which is at least 10-fold greater than that of a solubilized but unenriched membrane fraction from human 293 cells. More preferably, the compositions will have a β-secretase activity which is at least about 100-fold greater than that of the solubilized membrane fraction from human 293 cells. A specific method for determining β-secretase activity in units of "ng m$^{-1}$ h$^{-1}$" is described in detail in the Experimental section below (see footnote 1 to Table 1).

In addition to compositions comprising a naturally-occurring β-secretase molecule, the present invention comprises compositions including polypeptides comprising fragments of β-secretase as well as polypeptides substantially homologous to the intact β-secretase or a portion thereof. The β-secretase polypeptides of the present invention will generally exhibit at least about 80% sequence homology with the naturally-occurring sequence of the full-length β-secretase or an active fragment thereof, i.e., a fragment which displays APP cleavage activity. Usually, the β-secretase polypeptides will exhibit at least about 85% sequence homology, more usually at least about 95% sequence homology, and often 99% sequence homology or higher. The length of comparison sequences will generally be at least about 16 amino acid residues, usually at least about 20 residues, more usually at least about 24 residues, typically at least about 28 residues, and preferably more than about 35 residues.

The β-secretase polypeptides of the present invention may also be in the form of fusion polypeptides where an active fragment of the β-secretase molecule is joined to all or a portion of another protein. Fusions may be generated with heterologous proteins (for example, a reporter polypeptide, a binding polypeptide, or the like). Fusion polypeptides may be formed either recombinantly or by synthetic methods which are well-known in the art.

The β-secretase polypeptides of the present invention may also have amino acid residues which have been chemically modified by known techniques, such as phosphorylation, sulfonation, biotinylation or the addition of other moieties. In some embodiments, the modifications will be useful for labelling reagents, purification targets, affinity ligands targeting, or the like.

The β-secretase polypeptides of the present invention may be used to prepare polyclonal and/or monoclonal antibodies using conventional techniques with the β-secretase as an immunogen. The intact β-secretase molecule, or fragments thereof, optionally coupled to a carrier molecule, may be injected into small vertebrates, with monoclonal antibodies being produced by well-known methods. See, for example, Harlow and Lane (1988) *Antibodies: A Laboratory Manual,* Cold Spring Harbor Press, New York, and Goding (1986) *Monoclonal Antibodies: Principles and Practice* (2nd ed.) Academic Press, New York. Antibodies produced from β-secretase will be useful for performing conventional immunoassays to detect β-secretase in biological and other specimens.

The β-secretase compositions described above will be particularly useful for performing in vitro assays for detecting β-secretase inhibitors, where at least partially purified β-secretase is combined with the polypeptide substrate comprising the β-secretase cleavage site of APP in the presence of the test substrate. Conditions are maintained such that the β-secretase would cleave the polypeptide substrate into an amino-terminal fragment and a carboxy-terminal fragment in the absence of a substance which inhibits such cleavage. Cleavage of the polypeptide substrate in the presence of the test compound is compared with that in the absence of the test compound, and those test substances which provide significant inhibition of the cleavage activity (usually at least about 25% inhibition, more usually at least about 50% inhibition, preferably at least about 75% inhibition, and often at least about 90% inhibition or higher) are considered to be β-secretase inhibitors. Such β-secretase inhibitors may then be subjected to further in vitro and/or in vivo testing to determine if they inhibit the production of βAP in cellular and animal models. Suitable in vivo and in vitro tests are described in copending application Ser. Nos. 07/965,972 and 07/831,722, the full disclosures of which are incorporated herein by reference.

Suitable substrate polypeptides will include a region of the APP molecule which is recognized and cleaved by β-secretase. Usually, the substrate polypeptide will include at least about 15 amino acid residues, preferably at the least about 25 amino acids, on the amino-terminal side of the cleavage site (located between amino acids 596 and 597 in the 695-amino acid isomer) and at least about 28 amino acids, preferably at least about 42 amino acids, on the carboxy-terminal side of the cleavage site. The cleavage site will typically comprise the Met-Asp or the Leu-Asp cleavage site characteristic of the wild-type and Swedish forms of βAPP. An intact APP molecule will be suitable as the polypeptide including both wild-type and mutant forms of APP, particularly including the Swedish mutation of APP. Use of fusion substrate polypeptides is often preferred, where an affinity region can be fused to the β-secretase cleavage site of APP, producing a molecule whose cleavage can be conveniently monitored in solid phase test systems.

The screening assays of β-secretase and suitable substrate polypeptide are conveniently performed using "sandwich" assays where the amino-terminal or the carboxy-terminal fragment produced by cleavage is captured on a solid phase. The captured fragment may then be detected using an antibody specific for the end of the fragment exposed by β-secretase cleavage. In an exemplary embodiment described in detail in the Experimental section below, the polypeptide substrate is a fusion polypeptide combining maltose-binding protein and a 125-amino acid carboxy-terminal fragment of APP. The assay uses anti-maltose-binding protein antibody to capture the amino-terminal cleavage product, where the carboxy-terminus of the cleavage product is detected by an antibody specific thereto. An exemplary antibody is 192 antibody or SW-192 antibody, described in more detail in copending application Ser. No. 08/143,697, filed on Oct. 27, 1993, now U.S. Pat. No. 5,604,102, the full disclosure of which is incorporated herein by reference. The binding of the antibody to the cleaved fusion polypeptide is detected using conventional labelling systems, such as horseradish peroxidase or other detectable enzyme labels, which are bound to the antibody directly (covalently), or indirectly through intermediate linking substances, such as biotin and avidin.

The following examples are offered by way of illustration, not by way of limitation.

EXPERIMENTAL

Purification and Characterization of β-Secretase

Frozen tissue (293 cell paste or human brain) was cut into pieces and combined with five volumes of homogenization buffer (20 mM Hepes, pH 7.5, 0.25 M sucrose, 2 mM EDTA). The suspension was homogenized using a blender and centrifuged at 1000×g (10 min, 4° C.) to produce a post-nuclear supernatant which was saved on ice. The pellets were resuspended in fresh homogenizing buffer at the original volume, and the centrifugation step was repeated. The second supernatant was combined with the first one, and the supernatant pool ("PNS") was centrifuged at 16,000×g for 30 min at 4° C. The supernatants were discarded and the pellets, labelled "P2," were either used immediately for enzyme purification or frozen at −40° C. for later use.

The pellets were suspended in extraction buffer (20 mM MES, pH 6.0, 0.5% Triton X-100, 150 mM NaCl, 2 mM EDTA, 5 μg/ml leupeptin, 5 μg/ml E64, 1 μg/ml pepstatin, 0.2 mM PMSF) at the original volume. After vortex-mixing, the extraction was completed by agitating the tubes at 4° C. for a period of one hour. The mixtures were centrifuged as above at 16,000×g, and the supernatants were pooled. The pH of the extract was adjusted to 7.5 by adding ~1% (v/v) of 1 M Tris base (not neutralized).

The neutralized extract was loaded onto a wheat germ agglutinin-agarose (WGA-agarose) column pre-equilibrated with 10 column volumes of 20 mM Tris, pH 7.5, 0.5% Triton X-100, 150 mM NaCl, 2 mM EDTA, at 4° C. One milliliter of the agarose resin was used for every 4 g of original tissue used. The WGA-column was washed with 10 column volumes of the equilibration buffer, and then eluted as follows. Three-quarter column volumes of 1 M N-acetylglucosamine in 20 mM Tris, pH 7.5, 0.5% Triton X-100, 2 mM EDTA were passed through the column after which the flow was stopped for fifteen minutes. An additional five column volumes of the 1 M N-acetylglucosamine elution buffer were then used to elute the column, followed by five column volumes of 10% chitin hydrolysate in 20 mM Tris, pH 7.5, 0.5% Triton X-100, 2 mM EDTA. All of the above eluates were combined (pooled WGA-eluate).

The pooled WGA-eluate was diluted 1:4 with 20 mM NaOAc, pH 5.0, 0.5% Triton X-100, 2 mM EDTA. The pH of the diluted solution was adjusted to 5.0 by adding a few drops of glacial acetic acid while monitoring the pH. This "SP load" was passed through a 5-ml Pharmacia HiTrap SP-column equilibrated with 20 mM NaOAc, pH 5.0, 0.5% Triton X-100, 2 mM EDTA, at 4 ml/min at 4° C. β-Secretase activity was present in the flow-through fraction, which was neutralized by adding enough 1 M Tris (not neutralized) to bring the pH up to 7.5. The enzyme solution was then loaded onto a 1-ml Pharmacia HiTrap Q-column equilibrated with approximately 10 column volumes of 20 mM Tris, pH 7.5, 0.2% hydrogenated Triton X-100, 2 mM EDTA, at 1.5 ml/min at 4° C. The column was washed with 10 column volumes of 20 mM Tris, pH 7.5, 0.2% hydrogenated Triton X-100, 50 mM NaCl, 2 mM EDTA. Protein was eluted using a linear gradient from 50 mM TO 350 Mm NaCl over 30 minutes at a flow-rate of 1 ml/min at 4° C. The protein concentrations in the HiQ fractions were measured using a BioRad calorimetric protein assay, and the β-secretase activity was measured using the MBP-C125 cleavage assay at pH 5.5. The fractions in the ascending portion of the protein peak have the highest specific activity and were pooled for further purification of the enzyme.

The pooled fractions from the HiTrap Q were then applied to a column of concanavalin A-agarose (10% v/v of pool) equilibrated with 10 column volumes of 20 mM Tris, pH 7.5, 0.2% hydrogenated Triton X-100, 150 mM NaCl, 2 mM EDTA. The Con A flow-through was then loaded onto a Superdex 200 (26/60) gel exclusion chromatography column, which was eluted with phosphate buffered saline, pH 7.4, 0.2% hydrogenated Triton X-100, 2 mM EDTA, at 1 ml/min, collecting 3 min/fraction. Fractions containing β-secretase activity were identified using the MBP-C125 cleavage assay. The apparent molecular weight of the β-secretase activity eluting from the Superdex column was estimated from the peak elution volume (relative to that of standard proteins) to be 280,000±9800 (average of two runs for 293 cells, and two runs for human brain).

Results from a large-scale preparation of the enzyme from human brain tissue is shown in Table 1 below.

TABLE 1

| Step | Activity ng/ml/h | Protein μg/ml | Sp. Act.[1] ng/ml/h/μg protein | Fold Purfn. |
|---|---|---|---|---|
| Solubilized membrane extr. | 2700 | 350 | 7.7 | 1 |
| HiQ Elution pool | 80000 | 210 | 380.9 | 49.5 |
| Con A Flow-Thru | 80000 | 100 | 800 | 103.8 |
| Superdex peak fraction | 57000 | <5 | >11400 | >1480.5 |

$$\text{Sp. Act.} = \frac{(\text{Product conc. ng/ml}) (\text{Dilution factor}) (\text{Incubation vol. } \mu l)}{(\text{Enzyme sol. vol. } \mu l) (\text{Incubation time h.}) (\text{Enzyme conc. } \mu g/ml)}$$

The Sp. Act. is thus expressed as ng of protein produced per μg of β-secretase per hour.

Figure 3:
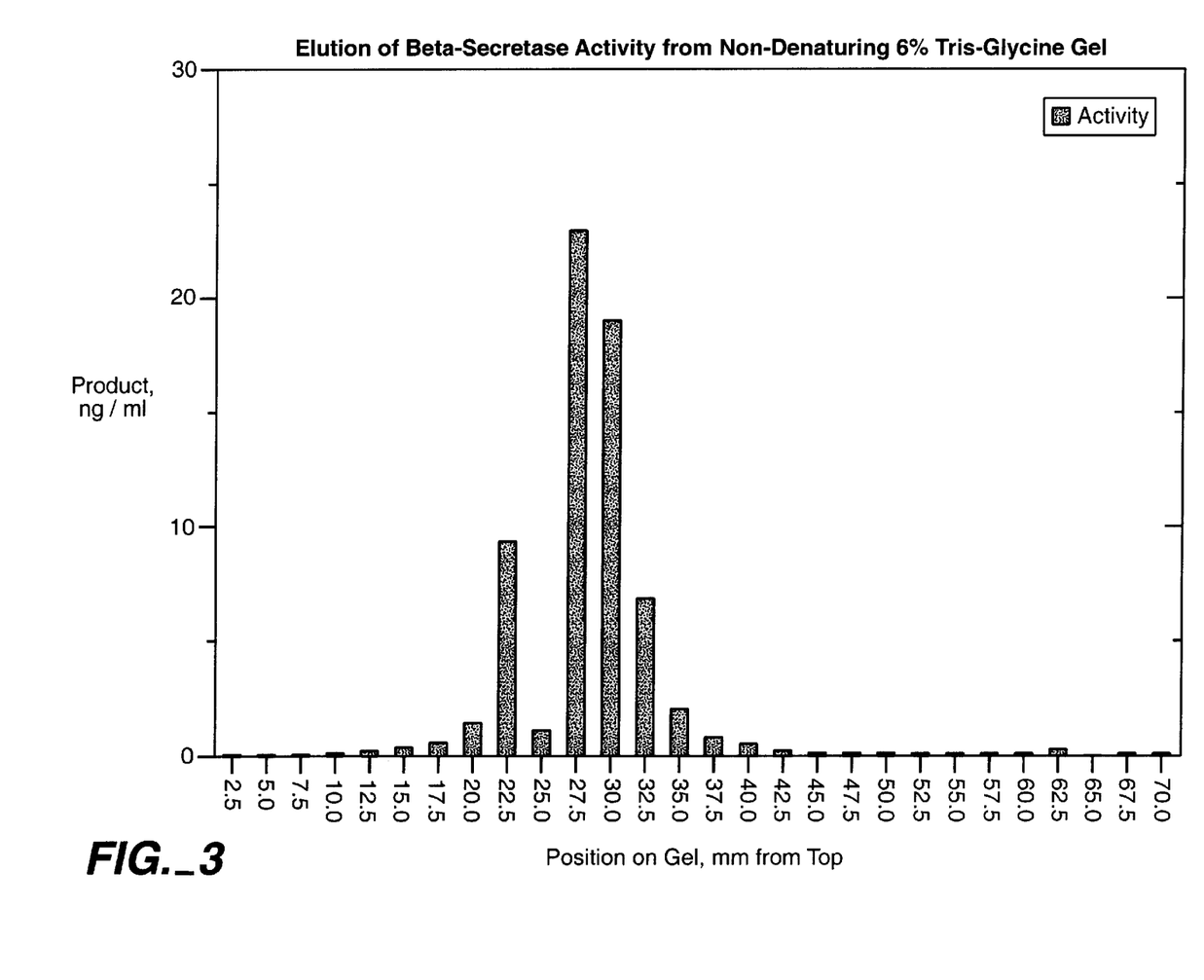
FIG. 3 is an electrophoretic gel elution profile of β-secretase activity.

In order to analyze for protein, a portion (360 μl) of each fraction was concentrated by acetone precipitation, then analyzed by SDS-PAGE and Coomassie blue staining on 10% Tris-Glycine gels. FIG. 1 shows the protein pattern of the Superdex 200 (26/60) elution profile for β-secretase purified from 293 cells, and FIG. 2 shows the elution profile for β-secretase purified from human brain. A number of protein bands are visible in the fractions with β-secretase activity. In order to further characterize the β-secretase, an aliquot of substantially purified β-secretase was electrophoresed under non-denaturing conditions into a 6% separating-4% stacking native gel system, according to the method of Laemmli (Nature, (1970) 227:680), except that the SDS is replaced by 0.2% hydrogenated triton X-100. Following electrophoresis, the gel is soaked for ~30 minutes in 0.1 M sodium acetate, pH 5.5. The lane of electrophoresed protein (7 cm long×1 cm wide×1 mm thick) is then cut into ~2.5 mm pieces using a clean razor blade, sequentially from the top of the stacker to the bottom of the separating gel. Each of these slices is combined with 60 μl water and 10 μl 1 M sodium acetate in a microcentrifuge tube, then homogenized using a Kontes Deltaware motorized pellet pestle microhomogenizer. MBP-C125 SW is added to the desired concentration (0.5–0.7 μg/ml), and the mixture incubated overnight. The samples are then diluted with Specimen Diluent (defined below) 50-fold, and analyzed by the β-secretase activity ELISA assay. The results are shown in FIG. 3.

Glycosylation of β-secretase has been investigated using various immobilized lectins, and ability of substantially purified β-secretase activity to bind to them was determined. Table 2 summarizes this data. A "−" sign signifies less than 20% binding, "+" between 24–40% binding, "++" between 50–75% binding, and "+++" >75% binding.

TABLE 2

| Lectin | β-Secretase Binding |
|---|---|
| jequirity bean (APA) | + |
| jack bean (con A) | + |
| scotch broom (CSA) | + |
| jimson weed (DSA) | + |
| coral tree (ECA) | − |

TABLE 2-continued

| Lectin | β-Secretase Binding |
|---|---|
| grifornia simplicifolia I | − |
| grifornia simplicifolia II | − |
| Jacalin (AIA) | + |
| lentil (LCA) | + |
| horseshoe crab (LPA) | − |
| tomato (LEL) | + |
| maackia (MAA) | + |
| peanut (PNA) | + |
| pokeweed (POA) | − |
| castor bean (RCA1) | − |
| potato (STL) | − |
| wheat germ - succinylated (SWGA) | + |
| China gourd (TKA) | + |
| stinging nettle (UDA) | + |
| gorse (UEAI) | − |
| gorse (UEAII) | − |
| hairy vetch (VVL) | − |
| wheat germ (WGA) | +++ |

Only a single lectin (WGA) bound β-secretase activity quantitatively, out of the many tested. Partial binding of the activity (25–40%) to a number of other lectins probably indicates heterogeneous glycosylation.

β-secretase purified as described was assayed in the presence of a number of common protease inhibitors as follows. Enzyme solution was mixed with the inhibitor, as described below in the β-Secretase Inhibitor Assay section, and assayed for activity remaining as a percentage of a control solution incubated under otherwise identical conditions. $IC_{50}$ values, if any, were determined as the concentration of inhibitor which resulted in 50% inhibition of the control activity. The results are set forth in Table 3.

TABLE 3

| Inhibitor | Max Conc | IC50 |
|---|---|---|
| SERINE PROTEASES | | |
| aminoethylbenzene-sulfonyl fluoride | 0.8 mM | NI |
| chymostatin | 0.2 mM | NI |
| 3,4-dichloroisocoumarin | 0.5 mM | <25% inh. |
| diisopropylfluoro-phosphate | 2 mM | NI |
| elastatinal | 0.2 mM | NI |
| phenylmethylsulfonyl-fluoride | 1.0 mM | NI |
| CYSTEINE PROTEASES | | |
| E-64 | 0.14 mM | NI |
| N-ethylmaleimide | 10 mM | NI |
| iodoacetamide | 10 mM | NI |
| METALLOPROTEASES | | |
| EDTA | 2 Mm | NI |
| phosphoramidon | 10 mM | NI |
| o-phenanthroline | | 7 mM |
| m-phenanthroline | | 7 mM |
| ASPARTYL PROTEASES | | |
| pepstatin | 25 μM | NI |
| diazoacetylnorleucyl-methyl ester | | >5 mM |
| DIVALENT METAL IONS | | |
| Cu | | 2 mM |
| Zn | | 3 mM |

TABLE 3-continued

| Inhibitor | Max Conc | IC50 |
|---|---|---|
| Hg | | <10% inh |
| Ca | | NI |
| Mg | | NI |

These results indicate that β-secretase activity is not inhibited by common inhibitors of serine, cysteine, aspartyl, and metalloproteases. Although o-phenanthroline inhibits poorly, m-phenanthroline, which is not a metal chelator, also does so, suggesting that this weak inhibition is unrelated to the metal-chelating properties of o-phenanthroline.

β-Secretase Inhibitor Assay

β-secretase assays utilizing the SW-192 antibody, which recognizes the free . . . Val-Asn-Leu-COOH terminal sequence uncovered proteolytic cleavage immediately amino-terminal of the βAP sequence, were performed. Two recombinantly-expressed proteins (FIGS. 4 and 5) have been used as substrates for β-secretase. The preferred substrate (FIG. 4) was expressed in E. coli as a fusion protein of the last 125 aa of APP fused to the carboxy-terminal end of maltose-binding protein, using commercially available vectors from New England Biolabs. The β-cleavage site was thus 26 amino acids downstream of the start of the C-125 region.

Figure 4:
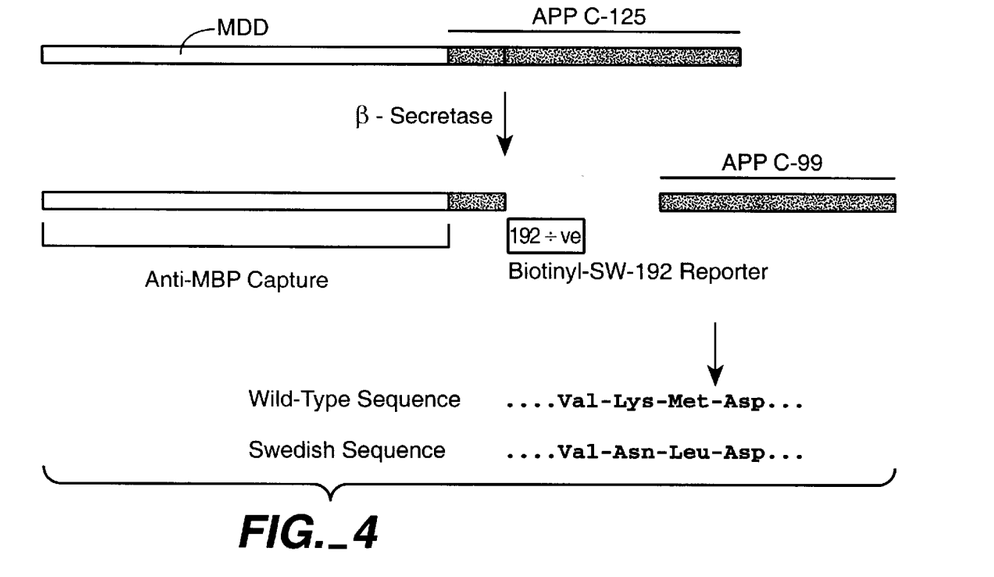
FIG. 4 is a schematic illustration of an APP-containing fusion peptide useful in performing the screening assays of the present invention, having a binding epitope derived from maltose-binding protein (MBP). An assay is run by exposing the fusion polypeptide to β-secretase which cleaves the 125 amino acid portion of APP (APP C-125) at the amino-terminus of the βAP. The MBP portion may then be captured, and the carboxy-terminus of the APP fragment which is exposed by cleavage with β-secretase may be identified with 192 antibody specific for said terminus.
Figure 5:
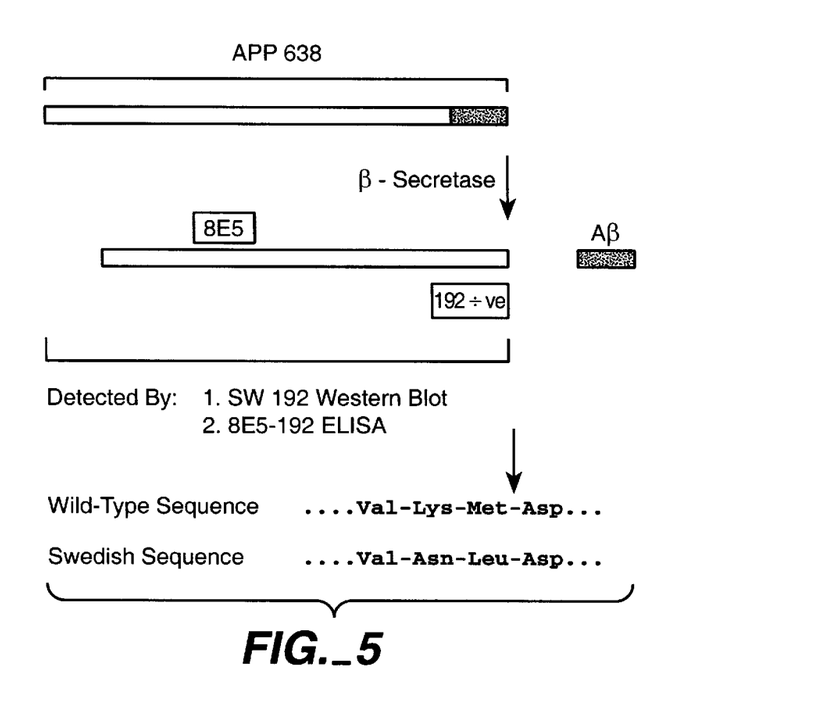
Figure 6B:
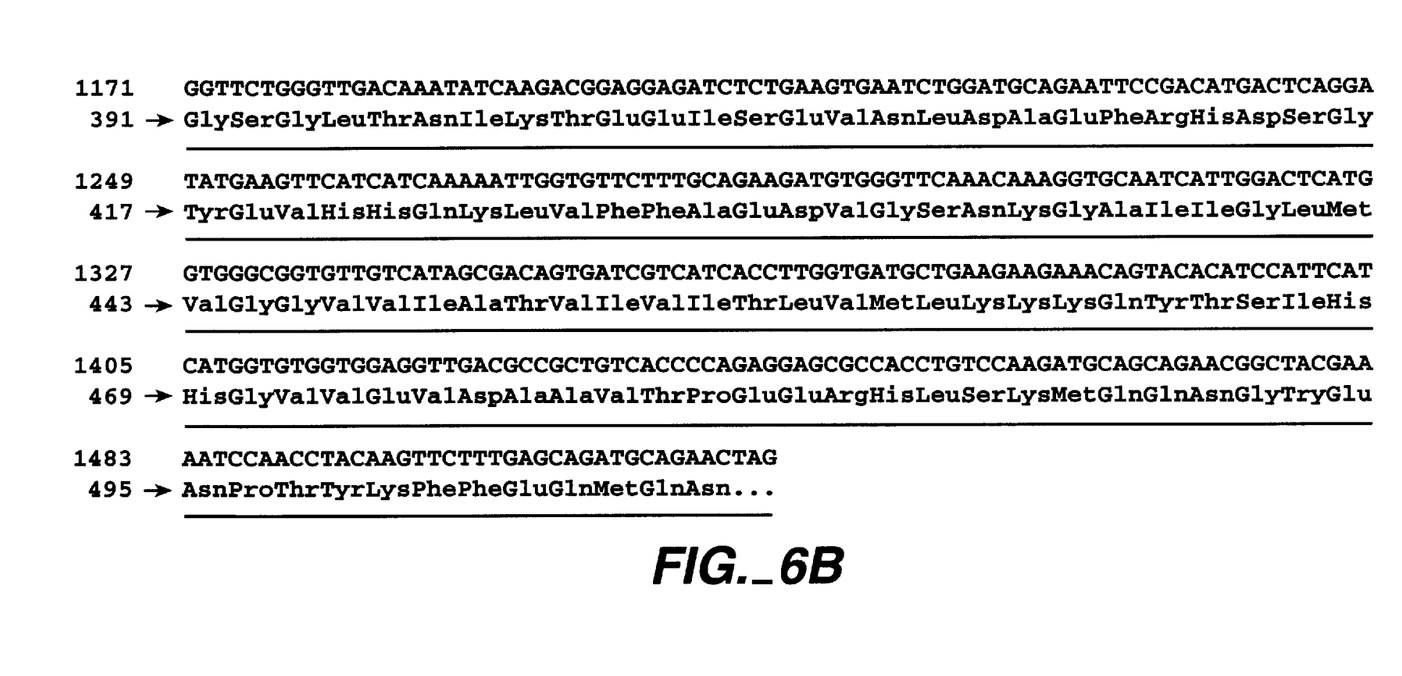
FIG. 6 is the complete amino acid sequence (nucleic acid sequence=SEQ ID NO:3; amino acid sequence=SEQ ID NO:4) of the Swedish mutation of the fusion polypeptide of maltose-binding protein and APP fragment utilized in the Experimental section hereinafter.

Recombinant proteins were generated with both the wild-type APP sequence (MBP-C125 WT) at the cleavage site (..Val-Lys-Met-Asp-Ala..) (SEQ ID No.:1) or the "Swedish" double mutation (MBP-C125 SW) (..Val-Asn-Leu-Asp-Ala..) [SEQ ID No.:2]. The entire sequence of the recombinant protein with the Swedish sequence is given in FIG. 6 [SEQ ID No.:3]. As shown in FIG. 4, cleavage of the intact MBP-fusion protein results in the generation of a truncated amino-terminal fragment, with the new SW-192 Ab-positive epitope uncovered at the carboxy terminus. This amino-terminal fragment can be recognized on Western blots with the same Ab, or, quantitatively, using an anti-MBP capture-biotinylated SW-192 reporter sandwich format, as shown in FIG. 4.

Anti-MBP polyclonal antibodies were raised in rabbits (Josman Labs, Berkeley) by immunization with purified recombinantly expressed MBP (New England Biolabs). Antisera were affinity purified on a column of immobilized MBP. MBP-C125 SW and WT substrates were expressed in E. coli, then purified using affinity binding to and elution from immobilized amylose-agarose matrix (New England Biolabs). The purified substrates were stored frozen at −40° C. in 3 M guaninide-HCl and 1% Triton X-100, @ ~0.7 mg/ml.

Figure 7:
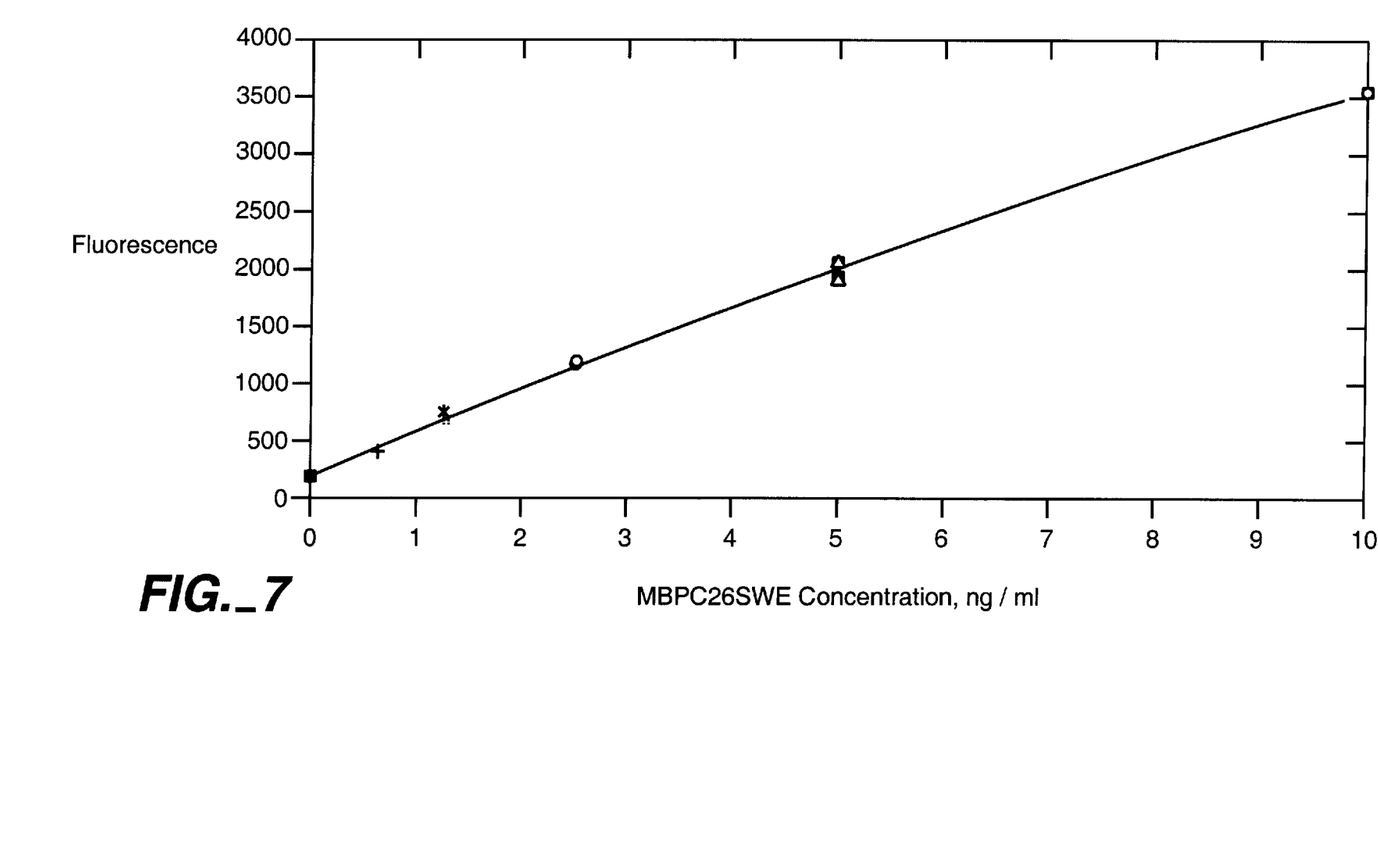
FIG. 7 is a standard curve generated for the β-secretase ELISA described in detail in the Experimental section below.

Microtiter 96-well plates were coated with purified anti-MBP antibody (@ 5–10 μg/ml), followed by blocking with human serum albumin. β-secretase solution (1–10 μl) is mixed with substrate (0.5 μl) in a final volume of 50 μl, with a final buffer composition of 20 mM sodium acetate, pH 5.5, 0.03% Triton X-100, in individual wells of 96-well microtiter plates, and incubated at 37° C. for 2 h. Samples were then diluted 5-fold with Specimen Diluent (0.2 g/l sodium phosphate monobasic, 2.15 g/l sodium phosphate dibasic, 0.5 g/l sodium azide, 8.5 g/l sodium chloride, 0.05% Triton X-405, 6 g/l BSA), further diluted 5–10 fold into Specimen Diluent on anti-MBP coated plates, and incubated for 1 h. Biotinylated SW192 antibodies were used as the reporter. SW192 polyclonal antibodies were biotinylated using NHS-biotin (Pierce), following the manufacturer's instruction. Usually, the biotinylated antibodies were used at about 240 ng/ml, the exact concentration varying with the lot of antibodies used. Following incubation of the plates with the reporter, the ELISA was developed using streptavidin-labeled alkaline phosphatase (Boeringer-Mannheim) and 4-methyl-umbelliferyl phosphate as fluorescent substrate. Plates were read in a Cytofluor 2350 Fluorescent Measurement System. Recombinantly generated MBP-26SW (product analog) was used as a standard to generate a standard curve (FIG. 7), which allowed the conversion of fluorescent units into amount of product generated.

This assay protocol was used to screen for inhibitor structures, using "libraries" of compounds assembled onto 96-well microtiter plates. Compounds were added, in a final concentration of 20 μg/ml in 2% DMSO, in the assay format described above, and the extent of product generated compared with control (2% DMSO only) β-secretase incubations, to calculate "% inhibition." "Hits" were defined as compounds which result in >35% inhibition of enzyme activity at test concentration. Using this system, 70 "hits" were identified out of the first 6336 compounds tested, a "hit" rate of ~1.1%. Thus, the assay has been shown to be capable of distinguishing "non-inhibitors" (the majority of compounds) from "inhibitors."

Although the foregoing invention has been described in some detail by way of illustration and example, for purposes of clarity of understanding, it will be obvious that certain changes and modifications may be practiced within the scope of the appended claims.

What is claimed is:

1. A method for determining whether a test substance inhibits proteolytic cleavage of β-amyloid precursor protein (APP) at the β-secretase cleavage site, comprising contacting said test substance with a partially purified β-secretase polypeptide characterized by (i) an apparent molecular weight when measured by gel exclusion chromatography in the range from 260 kilodaltons (kD) to 300 kD, and (ii) a specific activity that is at least five-fold greater than the specific activity of a solubilized but unenriched membrane fraction from human 293 cells, detecting cleavage of a substrate polypeptide which comprises (i) a β-secretase cleavage site, (ii) at least 15 amino acid residues on the amino-terminal side of said cleavage site derived from APP, and (iii) at least 28 amino acid residues on the carboxy-terminal side of said cleavage site derived from APP, and determining that said test substance inhibits said proteolytic cleavage, if cleavage of the substrate polypeptide at the β-secretase cleavage site by said β-secretase polypeptide is significantly reduced in the presence of said test substance compared to cleavage of said substrate polypeptide in the absence of said test substance.

2. The method of claim 1, wherein the specific activity of said β-secretase polypeptide is at least ten-fold higher than the specific activity of a solubilized but unenriched membrane fraction from human 293 cells.

3. The method of claim 1, wherein the specific activity of said β-secretase polypeptide is at least 100-fold higher than the specific activity of a solubilized but unenriched membrane fraction from human 293 cells.

4. The method of claim 1, wherein the specific activity of said β-secretase polypeptide is at least 1480-fold higher than the specific activity of a solubilized but unenriched membrane fraction from human 293 cells.

5. The method of claim 1, wherein said substrate polypeptide is derived from APP selected from the group consisting of human normal APP, the 770-amino acid isotype of APP and Swedish mutation APP.

6. The method of claim 1, wherein said substrate polypeptide comprises at least 25 amino acid residues on the amino-terminal side of said cleavage site derived from APP.

7. The method of claim 1, wherein said substrate polypeptide comprises at least 42 amino acid residues on the carboxy-terminal side of said cleavage site derived from APP.

8. The method of claim 1, wherein said substrate polypeptide comprises at least 25 amino acid residues on the amino-terminal side of said cleavage site and at least 42 amino acid residues on the carboxy-terminal side of said cleavage site.

9. The method of claim 1, wherein said substrate polypeptide comprises the 125 carboxy-terminal amino acids of APP.

10. The method of claim 9, wherein said polypeptide substrate is a fusion polypeptide comprising an amino-terminal portion having an antibody binding epitope and a carboxy terminal portion having said β-secretase cleavage site flanked by at least 15 amino acid residues on the amino-terminal side of said cleavage site and at least 28 amino acid residues on the carboxy-terminal side of said cleavage site.

11. The method of claim 9, wherein said polypeptide substrate is MBP-C125.

12. The method of claim 9, wherein said polypeptide substrate is APP.

13. The method of claim 1, wherein said cleavage of said polypeptide substrate is detected by detecting generation of at least one of an amino-terminal fragment or a carboxy-terminal fragment generated by said cleavage.

14. The method of claim 1, wherein said partially purified β-secretase polypeptide is characterized by an apparent molecular weight when measured by gel exclusion chromatography in the presence of 0.2% Triton-X100 in the range of 280±9.8 kD.

15. A method for determining whether a test substance inhibits proteolytic cleavage of β-amyloid precursor protein (APP) at the β-secretase cleavage site, comprising contacting said test substance with a partially purified β-secretase polypeptide characterized by (i) an apparent molecular weight when measured by gel exclusion chromatography in the range from 260 kilodaltons (kD) to 300 kD, and (ii) a specific activity that is at least 1480-fold greater than the specific activity of a solubilized but unenriched membrane fraction from human 293 cells, detecting cleavage of a substrate polypeptide which comprises (i) a β-secretase cleavage site, (ii) at least 15 amino acid residues on the amino-terminal side of said cleavage site derived from APP, and (iii) at least 28 amino acid residues on the carboxy-terminal side of said cleavage site derived from APP, and determining that said test substance inhibits said proteolytic cleavage, if cleavage of the substrate polypeptide at the β-secretase cleavage site by said β-secretase polypeptide is significantly reduced in the presence of said test substance compared to cleavage of said substrate polypeptide in the absence of said test substance.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 5 amino acids
       (B) TYPE: amino acid
       (C) STRANDEDNESS:
       (D) TOPOLOGY: linear     (ii) MOLECULE TYPE: peptide     (xi) SEQUENCE DESCRIPTION: SEQ ID NO:1:

Val Lys Met Asp Ala
1               5

(2) INFORMATION FOR SEQ ID NO:2:

(i) SEQUENCE CHARACTERISTICS:
       (A) LENGTH: 5 amino acids
       (B) TYPE: amino acid
       (C) STRANDEDNESS:
       (D) TOPOLOGY: linear     (ii) MOLECULE TYPE: peptide     (xi) SEQUENCE DESCRIPTION: SEQ ID NO:2:

Val Asn Leu Asp Ala
1               5

(2) INFORMATION FOR SEQ ID NO:3:

(i) SEQUENCE CHARACTERISTICS:
       (A) LENGTH: 1521 base pairs
       (B) TYPE: nucleic acid
       (C) STRANDEDNESS: single
       (D) TOPOLOGY: linear     (ii) MOLECULE TYPE: DNA     (ix) FEATURE:
       (A) NAME/KEY: CDS
       (B) LOCATION: 1..1521

(xi) SEQUENCE DESCRIPTION: SEQ ID NO:3:

```
ATG AAA ACT GAA GAA GGT AAA CTG GTA ATC TGG ATT AAC GGC GAT AAA      48
Met Lys Thr Glu Glu Gly Lys Leu Val Ile Trp Ile Asn Gly Asp Lys
 1               5                  10                  15

GGC TAT AAC GGT CTC GCT GAA GTC GGT AAG AAA TTC GAG AAA GAT ACC      96
```

-continued

| | | |
|---|---|---|
| Gly Tyr Asn Gly Leu Ala Glu Val Gly Lys Lys Phe Glu Lys Asp Thr<br>                 20                        25                        30 | | |
| GGA ATT AAA GTC ACC GTT GAG CAT CCG GAT AAA CTG GAA GAG AAA TTC<br>Gly Ile Lys Val Thr Val Glu His Pro Asp Lys Leu Glu Glu Lys Phe<br>        35                      40                      45 | 144 |
| CCA CAG GTT GCG GCA ACT GGC GAT GGC CCT GAC ATT ATC TTC TGG GCA<br>Pro Gln Val Ala Ala Thr Gly Asp Gly Pro Asp Ile Ile Phe Trp Ala<br>    50                      55                      60 | 192 |
| CAC GAC CGC TTT GGT GGC TAC GCT CAA TCT GGC CTG TTG GCT GAA ATC<br>His Asp Arg Phe Gly Gly Tyr Ala Gln Ser Gly Leu Leu Ala Glu Ile<br>65                      70                      75                      80 | 240 |
| ACC CCG GAC AAA GCG TTC CAG GAC AAG CTG TAT CCG TTT ACC TGG GAT<br>Thr Pro Asp Lys Ala Phe Gln Asp Lys Leu Tyr Pro Phe Thr Trp Asp<br>               85                      90                      95 | 288 |
| GCC GTA CGT TAC AAC GGC AAG CTG ATT GCT TAC CCG ATC GCT GTT GAA<br>Ala Val Arg Tyr Asn Gly Lys Leu Ile Ala Tyr Pro Ile Ala Val Glu<br>                  100                     105                  110 | 336 |
| GCG TTA TCG CTG ATT TAT AAC AAA GAT CTG CTG CCG AAC CCG CCA AAA<br>Ala Leu Ser Leu Ile Tyr Asn Lys Asp Leu Leu Pro Asn Pro Pro Lys<br>              115                     120                  125 | 384 |
| ACC TGG GAA GAG ATC CCG GCG CTG GAT AAA GAA CTG AAA GCG AAA GGT<br>Thr Trp Glu Glu Ile Pro Ala Leu Asp Lys Glu Leu Lys Ala Lys Gly<br>    130                      135                     140 | 432 |
| AAG AGC GCG CTG ATG TTC AAC CTG CAA GAA CCG TAC TTC ACC TGG CCG<br>Lys Ser Ala Leu Met Phe Asn Leu Gln Glu Pro Tyr Phe Thr Trp Pro<br>145                   150                     155                  160 | 480 |
| CTG ATT GCT GCT GAC GGG GGT TAT GCG TTC AAG TAT GAA AAC GGC AAG<br>Leu Ile Ala Ala Asp Gly Gly Tyr Ala Phe Lys Tyr Glu Asn Gly Lys<br>              165                     170                  175 | 528 |
| TAC GAC ATT AAA GAC GTG GGC GTG GAT AAC GCT GGC GCG AAA GCG GGT<br>Tyr Asp Ile Lys Asp Val Gly Val Asp Asn Ala Gly Ala Lys Ala Gly<br>                180                     185                  190 | 576 |
| CTG ACC TTC CTG GTT GAC CTG ATT AAA AAC AAA CAC ATG AAT GCA GAC<br>Leu Thr Phe Leu Val Asp Leu Ile Lys Asn Lys His Met Asn Ala Asp<br>            195                     200                  205 | 624 |
| ACC GAT TAC TCC ATC GCA GAA GCT GCC TTT AAT AAA GGC GAA ACA GCG<br>Thr Asp Tyr Ser Ile Ala Glu Ala Ala Phe Asn Lys Gly Glu Thr Ala<br>    210                      215                     220 | 672 |
| ATG ACC ATC AAC GGC CCG TGG GCA TGG TCC AAC ATC GAC ACC AGC AAA<br>Met Thr Ile Asn Gly Pro Trp Ala Trp Ser Asn Ile Asp Thr Ser Lys<br>225                   230                     235                  240 | 720 |
| GTG AAT TAT GGT GTA ACG GTA CTG CCG ACC TTC AAG GGT CAA CCA TCC<br>Val Asn Tyr Gly Val Thr Val Leu Pro Thr Phe Lys Gly Gln Pro Ser<br>                  245                     250                  255 | 768 |
| AAA CCG TTC GTT GGC GTG CTG AGC GCA GGT ATT AAC GCC GCC AGT CCG<br>Lys Pro Phe Val Gly Val Leu Ser Ala Gly Ile Asn Ala Ala Ser Pro<br>              260                     265                  270 | 816 |
| AAC AAA GAG CTG GCG AAA GAG TTC CTC GAA AAC TAT CTG CTG ACT GAT<br>Asn Lys Glu Leu Ala Lys Glu Phe Leu Glu Asn Tyr Leu Leu Thr Asp<br>            275                     280                  285 | 864 |
| GAA GGT CTG GAA GCG GTT AAT AAA GAC AAA CCG CTG GGT GCC GTA GCG<br>Glu Gly Leu Glu Ala Val Asn Lys Asp Lys Pro Leu Gly Ala Val Ala<br>    290                      295                     300 | 912 |
| CTG AAG TCT TAC GAG GAA GAG TTG GCG AAA GAT CCA CGT ATT GCC GCC<br>Leu Lys Ser Tyr Glu Glu Glu Leu Ala Lys Asp Pro Arg Ile Ala Ala<br>305                   310                     315                  320 | 960 |
| ACC ATG GAA AAC GCC CAG AAA GGT GAA ATC ATG CCG AAC ATC CCG CAG<br>Thr Met Glu Asn Ala Gln Lys Gly Glu Ile Met Pro Asn Ile Pro Gln<br>            325                     330                  335 | 1008 |

```
ATG TCC GCT TTC TGG TAT GCC GTG CGT ACT GCG GTG ATC AAC GCC GCC        1056
Met Ser Ala Phe Trp Tyr Ala Val Arg Thr Ala Val Ile Asn Ala Ala
        340                 345                 350

AGC GGT CGT CAG ACT GTC GAT GAA GCC CTG AAA GAC GCG CAG ACT AAT        1104
Ser Gly Arg Gln Thr Val Asp Glu Ala Leu Lys Asp Ala Gln Thr Asn
            355                 360                 365

TCG AGC TCG GTA CCC GGC CGG GGA TCC ATC GAG GGT AGG GCC GAC CGA        1152
Ser Ser Ser Val Pro Gly Arg Gly Ser Ile Glu Gly Arg Ala Asp Arg
370                 375                 380

GGA CTG ACC ACT CGA CCA GGT TCT GGG TTG ACA AAT ATC AAG ACG GAG        1200
Gly Leu Thr Thr Arg Pro Gly Ser Gly Leu Thr Asn Ile Lys Thr Glu
385                 390                 395                 400

GAG ATC TCT GAA GTG AAT CTG GAT GCA GAA TTC CGA CAT GAC TCA GGA        1248
Glu Ile Ser Glu Val Asn Leu Asp Ala Glu Phe Arg His Asp Ser Gly
            405                 410                 415

TAT GAA GTT CAT CAT CAA AAA TTG GTG TTC TTT GCA GAA GAT GTG GGT        1296
Tyr Glu Val His His Gln Lys Leu Val Phe Phe Ala Glu Asp Val Gly
            420                 425                 430

TCA AAC AAA GGT GCA ATC ATT GGA CTC ATG GTG GGC GGT GTT GTC ATA        1344
Ser Asn Lys Gly Ala Ile Ile Gly Leu Met Val Gly Gly Val Val Ile
        435                 440                 445

GCG ACA GTG ATC GTC ATC ACC TTG GTG ATG CTG AAG AAG AAA CAG TAC        1392
Ala Thr Val Ile Val Ile Thr Leu Val Met Leu Lys Lys Lys Gln Tyr
450                 455                 460

ACA TCC ATT CAT CAT GGT GTG GTG GAG GTT GAC GCC GCT GTC ACC CCA        1440
Thr Ser Ile His His Gly Val Val Glu Val Asp Ala Ala Val Thr Pro
465                 470                 475                 480

GAG GAG CGC CAC CTG TCC AAG ATG CAG CAG AAC GGC TAC GAA AAT CCA        1488
Glu Glu Arg His Leu Ser Lys Met Gln Gln Asn Gly Tyr Glu Asn Pro
            485                 490                 495

ACC TAC AAG TTC TTT GAG CAG ATG CAG AAC TAG                            1521
Thr Tyr Lys Phe Phe Glu Gln Met Gln Asn
                500                 505
```

(2) INFORMATION FOR SEQ ID NO:4:

(i) SEQUENCE CHARACTERISTICS:
        (A) LENGTH: 506 amino acids
        (B) TYPE: amino acid
        (D) TOPOLOGY: linear     (ii) MOLECULE TYPE: protein     (xi) SEQUENCE DESCRIPTION: SEQ ID NO:4:

```
Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125
```

```
Thr Trp Glu Glu Ile Pro Ala Leu Asp Lys Glu Leu Lys Ala Lys Gly
    130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
                180                 185                 190
Leu Thr Phe Leu Val Asp Leu Ile Lys Asn Lys His Met Asn Ala Asp
                195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
    275                 280                 285
Glu Gly Leu Glu Ala Val Asn Lys Asp Lys Pro Leu Gly Ala Val Ala
    290                 295                 300
Leu Lys Ser Tyr Glu Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
    355                 360                 365
Ser Ser Ser Val Pro Gly Arg Gly Ser Ile Glu Gly Arg Ala Asp Arg
    370                 375                 380
Gly Leu Thr Thr Arg Pro Gly Ser Gly Leu Thr Asn Ile Lys Thr Glu
385                 390                 395                 400
Glu Ile Ser Glu Val Asn Leu Asp Ala Glu Phe Arg His Asp Ser Gly
                405                 410                 415
Tyr Glu Val His His Gln Lys Leu Val Phe Phe Ala Glu Asp Val Gly
                420                 425                 430
Ser Asn Lys Gly Ala Ile Ile Gly Leu Met Val Gly Gly Val Val Ile
    435                 440                 445
Ala Thr Val Ile Val Ile Thr Leu Val Met Leu Lys Lys Lys Gln Tyr
    450                 455                 460
Thr Ser Ile His His Gly Val Val Glu Val Asp Ala Ala Val Thr Pro
465                 470                 475                 480
Glu Glu Arg His Leu Ser Lys Met Gln Gln Asn Gly Tyr Glu Asn Pro
                485                 490                 495
Thr Tyr Lys Phe Phe Glu Gln Met Gln Asn
                500                 505
```

(2) INFORMATION FOR SEQ ID NO:5:

(i) SEQUENCE CHARACTERISTICS:
        (A) LENGTH: 4 amino acids
        (B) TYPE: amino acid

```
        (C) STRANDEDNESS:
        (D) TOPOLOGY: linear (ii) MOLECULE TYPE: peptide (xi) SEQUENCE DESCRIPTION: SEQ ID NO:5:

Val Lys Met Asp
1

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Val Asn Leu Asp
1
```